United States Patent
Michelson

(10) Patent No.: US 7,540,882 B2
(45) Date of Patent: *Jun. 2, 2009

(54) ARTIFICIAL SPINAL FUSION IMPLANT WITH ASYMMETRICAL LEADING END

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 209 days.

This patent is subject to a terminal disclaimer.

(21) Appl. No.: 11/089,057

(22) Filed: Mar. 24, 2005

(65) Prior Publication Data

US 2005/0187628 A1    Aug. 25, 2005

Related U.S. Application Data

(63) Continuation of application No. 10/112,747, filed on Apr. 2, 2002, now Pat. No. 6,890,355.

(60) Provisional application No. 60/281,187, filed on Apr. 3, 2001, provisional application No. 60/281,124, filed on Apr. 2, 2001.

(51) Int. Cl.
*A61F 2/44* (2006.01)
*A61B 17/70* (2006.01)

(52) U.S. Cl. .................. 623/17.11; 623/17.16; 606/247

(58) Field of Classification Search .................. 606/61, 606/247; 623/17.11–17.16
See application file for complete search history.

(56) References Cited

U.S. PATENT DOCUMENTS

| 2,677,369 A | 5/1954 | Knowles |
| 3,848,601 A | 11/1974 | Ma et al. |
| 3,867,728 A | 2/1975 | Stubstad et al. |
| 3,875,595 A | 4/1975 | Froning |
| 3,905,047 A | 9/1975 | Long |
| D245,259 S | 8/1977 | Shen |
| 4,070,514 A | 1/1978 | Eatherly et al. |
| 4,309,777 A | 1/1982 | Patil |
| 4,349,921 A | 9/1982 | Kuntz |
| 4,501,269 A | 2/1985 | Bagby |
| RE31,865 E | 4/1985 | Roux |
| 4,599,086 A | 7/1986 | Doty |

(Continued)

FOREIGN PATENT DOCUMENTS

EP    0077159    4/1983

(Continued)

OTHER PUBLICATIONS

Crock, H.V.; Practice of Spinal Surgery; Springer-Verlag/Wien, New York (1983).

(Continued)

*Primary Examiner*—Pedro Philogene
(74) *Attorney, Agent, or Firm*—Martin & Ferraro, LLP

(57) ABSTRACT

An interbody spinal implant made of a material other than bone adapted for placement across an intervertebral space formed across the height of a disc space between two adjacent vertebral bodies. The implant has a leading end that includes at least a portion of an arc of a circle from side to side, and sides that are at least in part straight or a trailing end having a radius of curvature of another circle from side to side.

29 Claims, 6 Drawing Sheets

U.S. PATENT DOCUMENTS

| | | | |
|---|---|---|---|
| 4,636,217 A | | 1/1987 | Ogilvie et al. |
| 4,714,469 A * | | 12/1987 | Kenna .................. 606/61 |
| 4,743,256 A | | 5/1988 | Brantigan |
| 4,759,766 A | | 7/1988 | Buettner-Janz et al. |
| 4,759,769 A | | 7/1988 | Hedman et al. |
| 4,820,305 A | | 4/1989 | Harms et al. |
| 4,834,757 A | | 5/1989 | Brantigan |
| 4,863,477 A | | 9/1989 | Monson |
| 4,877,020 A | | 10/1989 | Vich |
| 4,878,915 A | | 11/1989 | Brantigan |
| 4,904,261 A | | 2/1990 | Dove et al. |
| 4,911,718 A | | 3/1990 | Lee et al. |
| 4,936,848 A | | 6/1990 | Bagby |
| 4,955,908 A | | 9/1990 | Frey et al. |
| 5,015,247 A | | 5/1991 | Michelson |
| 5,015,255 A | | 5/1991 | Kuslich |
| 5,047,055 A | | 9/1991 | Bao et al. |
| 5,059,193 A | | 10/1991 | Kuslich |
| 5,062,845 A | | 11/1991 | Kuslich et al. |
| 5,071,437 A | | 12/1991 | Steffee |
| 5,122,130 A | | 6/1992 | Keller |
| 5,123,926 A | | 6/1992 | Pisharodi |
| 5,192,327 A * | | 3/1993 | Brantigan ............. 623/17.11 |
| 5,246,458 A | | 9/1993 | Graham |
| 5,258,031 A | | 11/1993 | Salib et al. |
| 5,306,308 A | | 4/1994 | Gross et al. |
| 5,306,309 A | | 4/1994 | Wagner et al. |
| 5,370,697 A | | 12/1994 | Baumgartner |
| 5,397,364 A | | 3/1995 | Kozak et al. |
| 5,423,855 A | | 6/1995 | Marienne |
| 5,425,772 A | | 6/1995 | Brantigan |
| 5,443,514 A | | 8/1995 | Steffee |
| 5,458,638 A | | 10/1995 | Kuslich et al. |
| 5,507,813 A | | 4/1996 | Dowd et al. |
| 5,571,109 A | | 11/1996 | Bertagnoli |
| D377,527 S | | 1/1997 | Michelson |
| 5,609,635 A | | 3/1997 | Michelson |
| 5,645,084 A | | 7/1997 | McKay |
| 5,669,909 A | | 9/1997 | Zdeblick et al. |
| 5,683,463 A | | 11/1997 | Godefroy et al. |
| 5,702,449 A | | 12/1997 | McKay |
| 5,766,252 A | | 6/1998 | Henry et al. |
| 5,776,199 A | | 7/1998 | Michelson |
| 5,782,919 A | | 7/1998 | Zdeblick et al. |
| D397,439 S | | 8/1998 | Koros et al. |
| 5,800,547 A | | 9/1998 | Schafer et al. |
| 5,814,084 A | | 9/1998 | Grivas et al. |
| 5,846,484 A | | 12/1998 | Scarborough et al. |
| 5,855,227 A * | | 1/1999 | Stucchi .................. 137/614.03 |
| 5,861,041 A | | 1/1999 | Tienboon |
| 5,865,845 A | | 2/1999 | Thalgott |
| 5,888,222 A | | 3/1999 | Coates et al. |
| 5,888,226 A | | 3/1999 | Rogozinski |
| 5,888,227 A * | | 3/1999 | Cottle .................. 623/17.16 |
| 5,899,939 A | | 5/1999 | Boyce et al. |
| 5,906,635 A | | 5/1999 | Maniglia |
| 5,972,368 A | | 10/1999 | McKay |
| 5,989,289 A | | 11/1999 | Coates et al. |
| 6,033,438 A | | 3/2000 | Bianchi et al. |
| 6,037,519 A | | 3/2000 | McKay |
| 6,039,762 A | | 3/2000 | McKay |
| D425,989 S | | 5/2000 | Michelson |
| 6,083,228 A | | 7/2000 | Michelson |
| 6,111,164 A | | 8/2000 | Rainey et al. |
| 6,113,638 A | | 9/2000 | Williams et al. |
| 6,136,031 A | | 10/2000 | Middleton |
| 6,143,032 A | | 11/2000 | Schafer et al. |
| 6,174,311 B1 | | 1/2001 | Branch et al. |
| 6,179,875 B1 | | 1/2001 | Von Strempel |
| 6,200,347 B1 | | 3/2001 | Anderson et al. |
| 6,206,923 B1 | | 3/2001 | Boyd et al. |
| 6,224,607 B1 | | 5/2001 | Michelson |
| 6,231,610 B1 | | 5/2001 | Geisler |
| 6,241,770 B1 | | 6/2001 | Michelson |
| 6,241,771 B1 | | 6/2001 | Gresser et al. |
| 6,245,108 B1 * | | 6/2001 | Biscup .................. 623/17.11 |
| 6,258,125 B1 | | 7/2001 | Paul et al. |
| 6,261,586 B1 | | 7/2001 | McKay |
| 6,270,528 B1 | | 8/2001 | McKay |
| 6,277,149 B1 | | 8/2001 | Boyle et al. |
| 6,294,041 B1 | | 9/2001 | Boyce et al. |
| 6,294,187 B1 | | 9/2001 | Boyce et al. |
| 6,342,074 B1 | | 1/2002 | Simpson |
| 6,348,071 B1 | | 2/2002 | Steffee et al. |
| 6,350,283 B1 | | 2/2002 | Michelson |
| 6,371,988 B1 | | 4/2002 | Pafford et al. |
| 6,383,221 B1 | | 5/2002 | Scarborough et al. |
| 6,395,031 B1 | | 5/2002 | Foley et al. |
| 6,402,785 B1 | | 6/2002 | Zdeblick et al. |
| 6,409,765 B1 | | 6/2002 | Bianchi et al. |
| 6,423,095 B1 | | 7/2002 | Van Hoeck et al. |
| 6,425,108 B1 * | | 7/2002 | Chiang .................. 714/764 |
| 6,468,311 B2 | | 10/2002 | Boyd et al. |
| 6,471,724 B2 | | 10/2002 | Zdeblick et al. |
| 6,482,233 B1 | | 11/2002 | Aebl et al. |
| 6,511,509 B1 | | 1/2003 | Ford et al. |
| 6,530,955 B2 | | 3/2003 | Boyle et al. |
| 6,554,863 B2 | | 4/2003 | Paul et al. |
| 6,562,072 B1 | | 5/2003 | Fuss et al. |
| 6,572,654 B1 | | 6/2003 | Santilli |
| 6,629,998 B1 * | | 10/2003 | Lin .................. 623/17.11 |
| 6,635,086 B2 | | 10/2003 | Lin |
| 6,749,636 B2 | | 6/2004 | Michelson |
| 6,808,585 B2 | | 10/2004 | Boyce et al. |
| 6,890,355 B2 * | | 5/2005 | Michelson ............. 623/17.11 |
| 6,989,031 B2 | | 1/2006 | Michelson |
| 7,048,762 B1 | | 5/2006 | Sander et al. |
| 7,087,082 B2 | | 8/2006 | Paul et al. |
| 7,115,146 B2 | | 10/2006 | Boyer |
| 2001/0018614 A1 | | 8/2001 | Bianchi |
| 2001/0031254 A1 | | 10/2001 | Bianchi et al. |
| 2002/0091447 A1 | | 7/2002 | Shimp et al. |
| 2002/0099444 A1 | | 7/2002 | Boyd et al. |
| 2002/0107571 A1 | | 8/2002 | Foley |
| 2003/0028249 A1 | | 2/2003 | Baccelli et al. |
| 2003/0120344 A1 | | 6/2003 | Michelson |

FOREIGN PATENT DOCUMENTS

| | | |
|---|---|---|
| EP | 0179695 | 4/1986 |
| EP | 0307241 | 3/1989 |
| EP | 0577179 | 1/1994 |
| EP | 0599419 | 6/1994 |
| EP | 0627204 | 12/1994 |
| EP | 0637440 | 11/1997 |
| FR | 2703580 | 10/1994 |
| JP | 57/029348 | 9/1982 |
| JP | 62/155846 | 7/1987 |
| WO | WO 93/01771 | 2/1993 |
| WO | WO 95/08306 | 3/1995 |
| WO | WO 95/08964 | 4/1995 |
| WO | WO 96/22747 | 8/1996 |
| WO | WO 99/63891 | 12/1999 |
| WO | WO 00/74608 | 12/2000 |
| WO | WO 01/28465 | 4/2001 |
| WO | WO 01/68005 | 4/2001 |
| WO | WO 01/62191 | 8/2001 |
| WO | WO 01/68004 | 9/2001 |

OTHER PUBLICATIONS

Itoman, M., et al.; Banked Bone grafting for Bone Defect Repair-Clinical Evaluation of Bone Union and Graft Incorporation; J. Jpn. Orthop. Assoc. 62:461-469 (1988).

Laparoscopic Bone Dowel Surgical Technique; Brochure of Sofamor Danek (1995).

Brochure of University of Florida Tissue Bank; MD-I and MD-II Custom Machine Cortical Dowels; (Circa 1996).

Brochure of University of Florida Tissue Bank; MD-III Threaded Cortical Dowel; (Circa 1996).

Ray, C.D.; Spinal Interbody Fusions: A Review, Featuring New Generation Techniques; Neurosurgery Quarterly, 7(2):135-156 (1997).

A picture of a Medtronic, Sofamor Danek Display; titled "Evolving With Your Needs" (Apr. 2000).

RTI Precision Machined Allograft: The Surgeon's Choice, Brochure by Regeneration Technologies, Inc. (2000).

Puros ALIF Bone Graft, Brochure by Sulzer Spine-Tech (2001).

What's New at . . . Spine-Tech: Allograft and Thoracolumbar, Brochure Spine-Tech (Circa 2001).

New IBS Allograft, The C-TLIF Approach, Brochure of OrthoDevelopment (2002).

Introducing graftech Allografts, Webpage by Osteotech (Circa Jan. 2002).

RTI Tissue Services, Spinal Allograft, Webpage of Regeneration Technologies, Inc. (2002).

DeBowes, R.M., et al.; Study of Bovine . . . Steel Baskets; Transactions of the 29th Annual Meeting; Orthopedic Research Society, vol. 8, p. 407, (Mar. 8-10, 1983).

Otero-Vich, Jose M.; Anterior Cervical Interbody Fusion with Threaded Cylinrical Bone; J. Neurosurg 63:750-753 (Nov. 1985).

Schmitz et al.; Performance of Alloplastic Materials and Design of an Artificial Disc; the Artificial Disc. Brock, Mayer, Weigel; pp. 23-24 (1991).

Zindrick, et al.; Lumbar Spine Fusion: Different Types and Indications; The Lumbar Spine, vol. 1, Second Edition, pp. 588-593 (1996).

U.S. Appl. No. 09/593,591, filed Jun. 2000, Michelson.

Muschler, et al.; The Biology of Spinal Fusion; Spinal Fusion Science and Technique, Cotler and Cotler, pp. 9-13 (Dec. 1989).

* cited by examiner

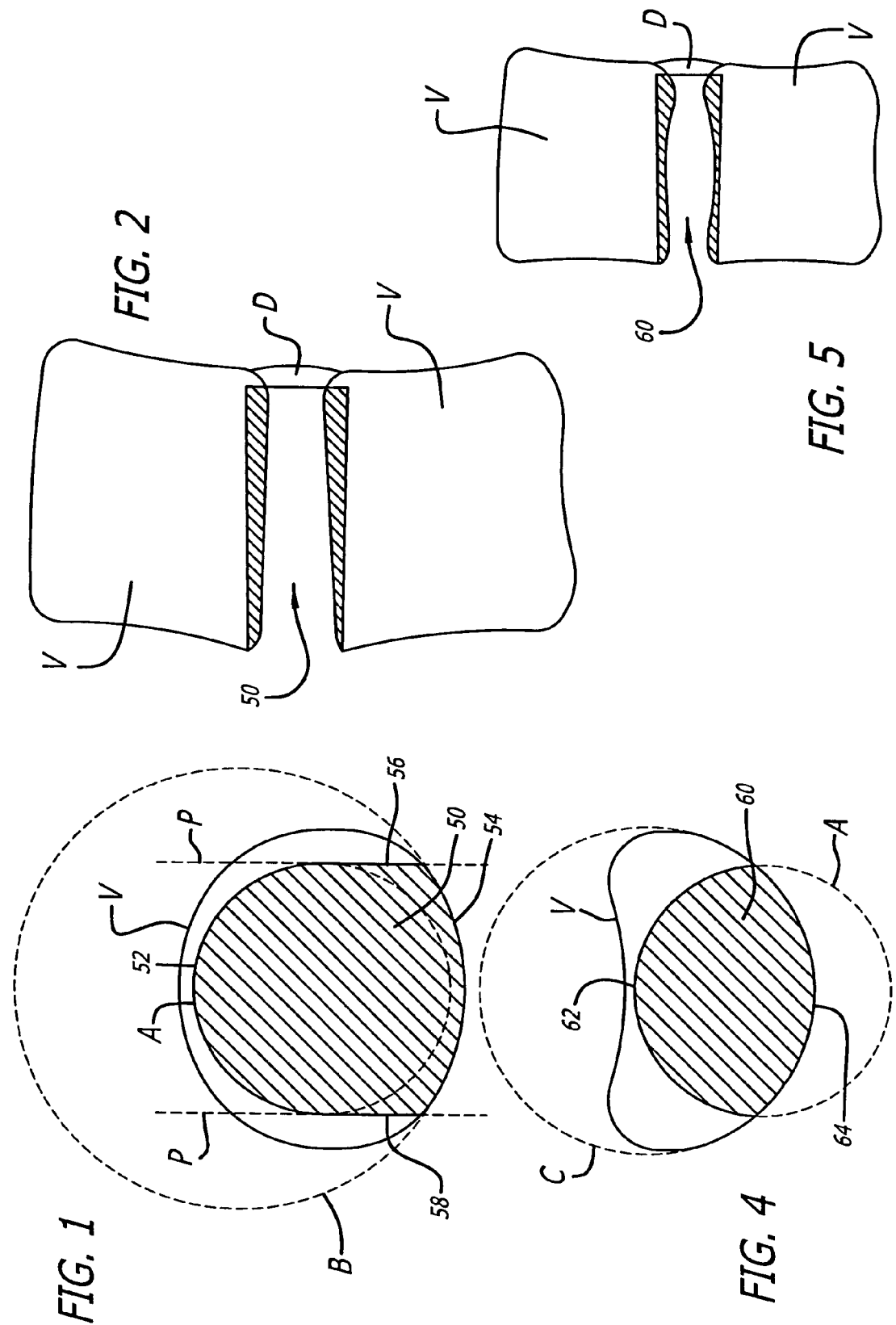

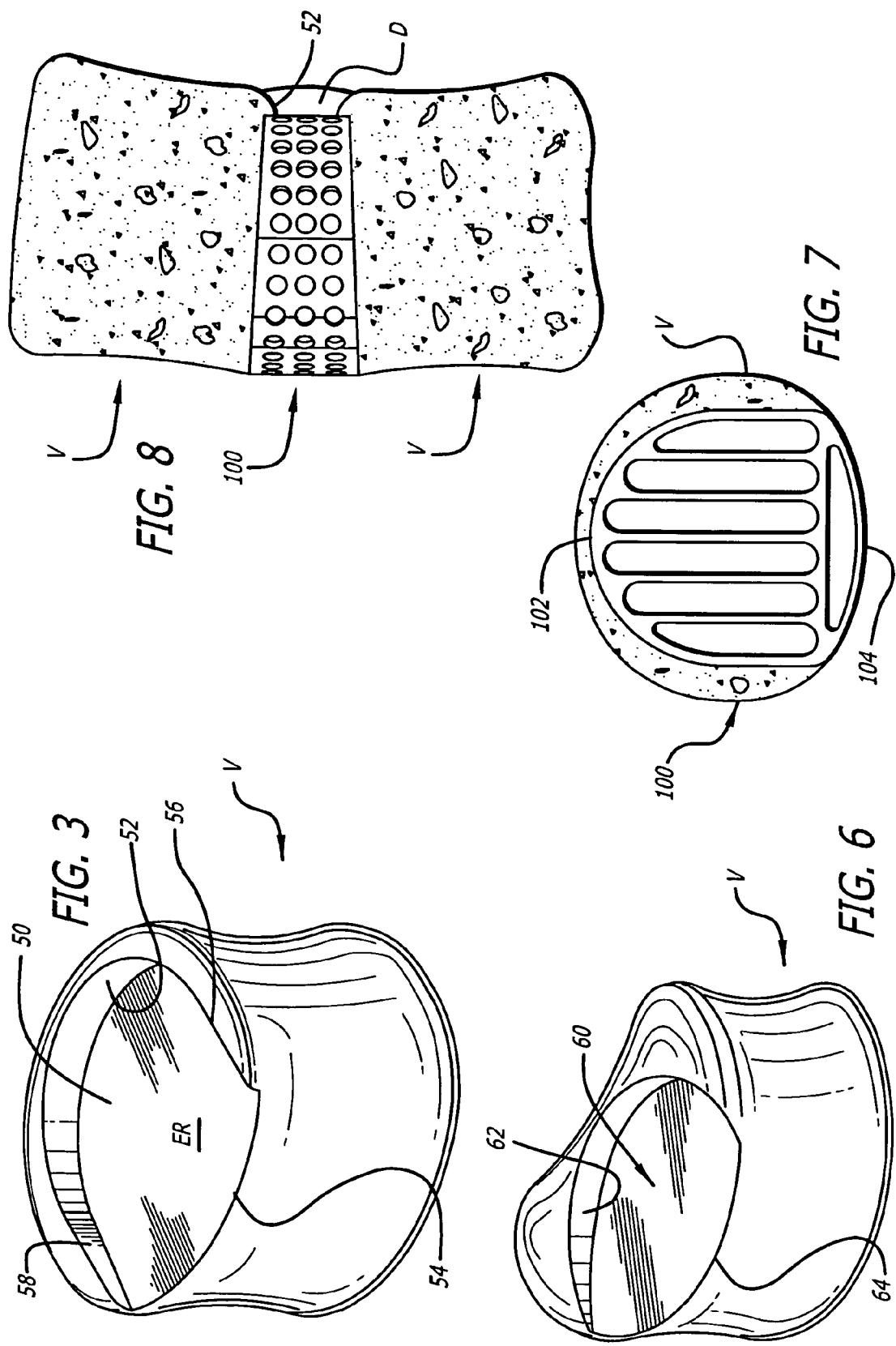

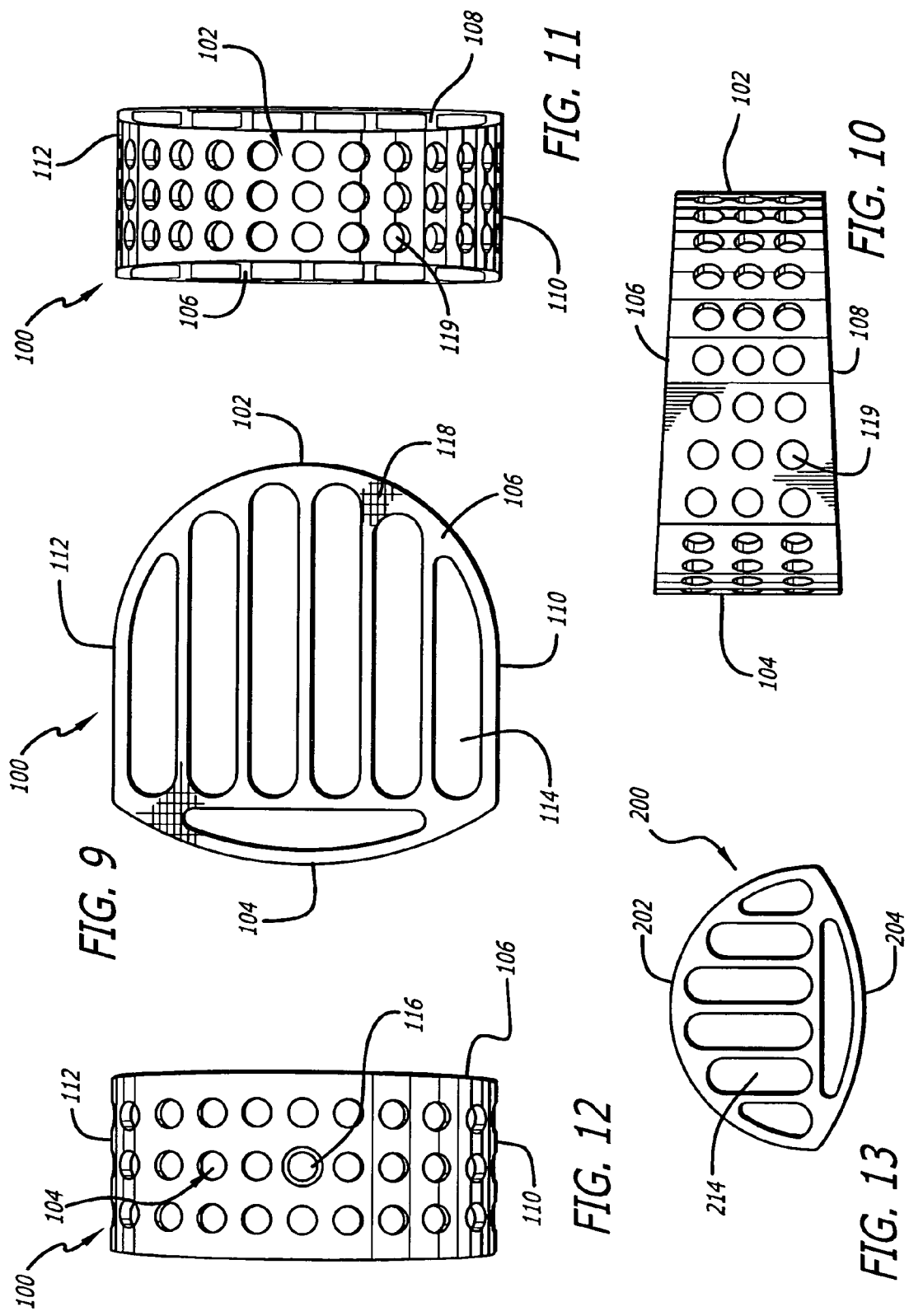

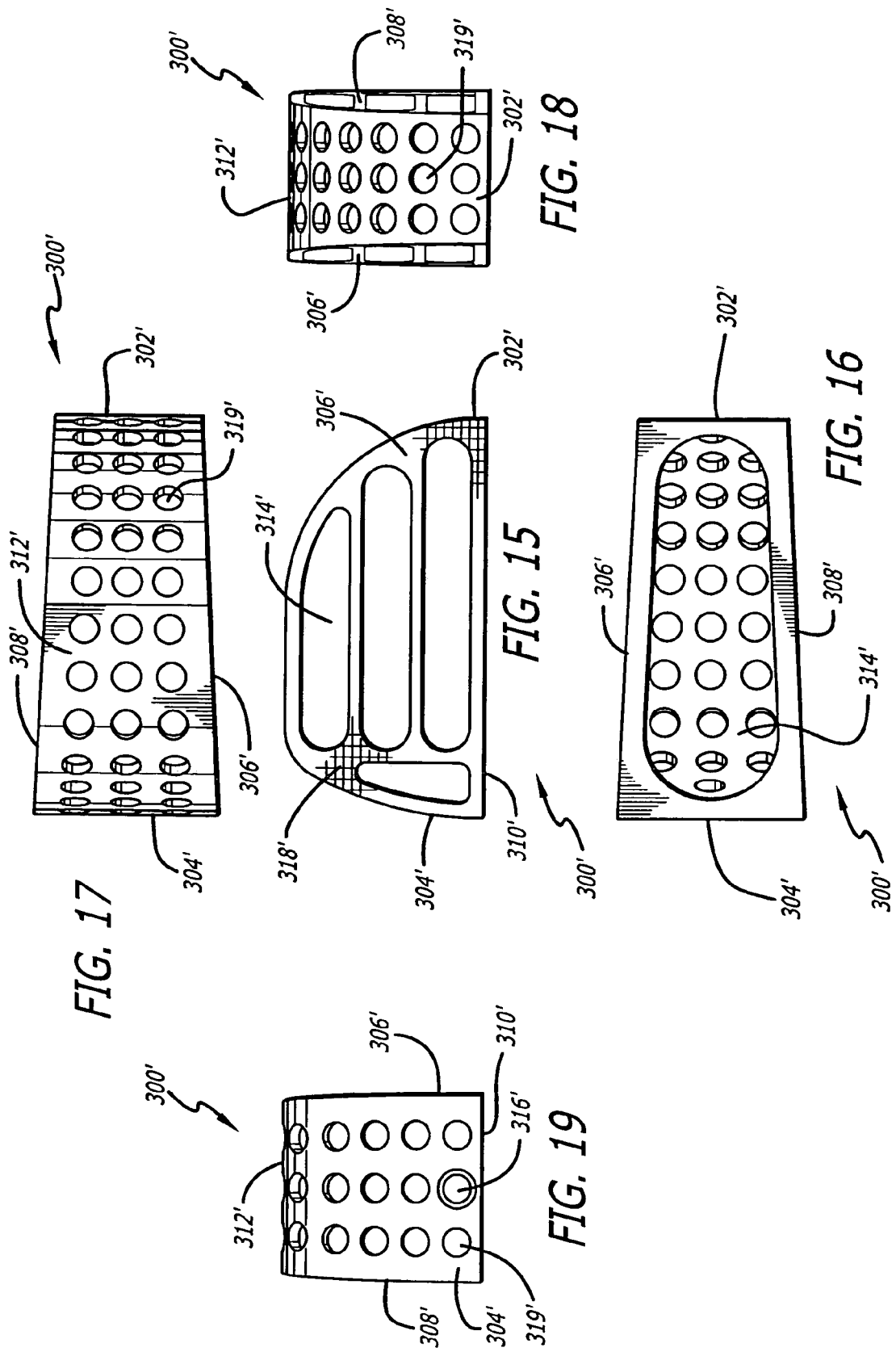

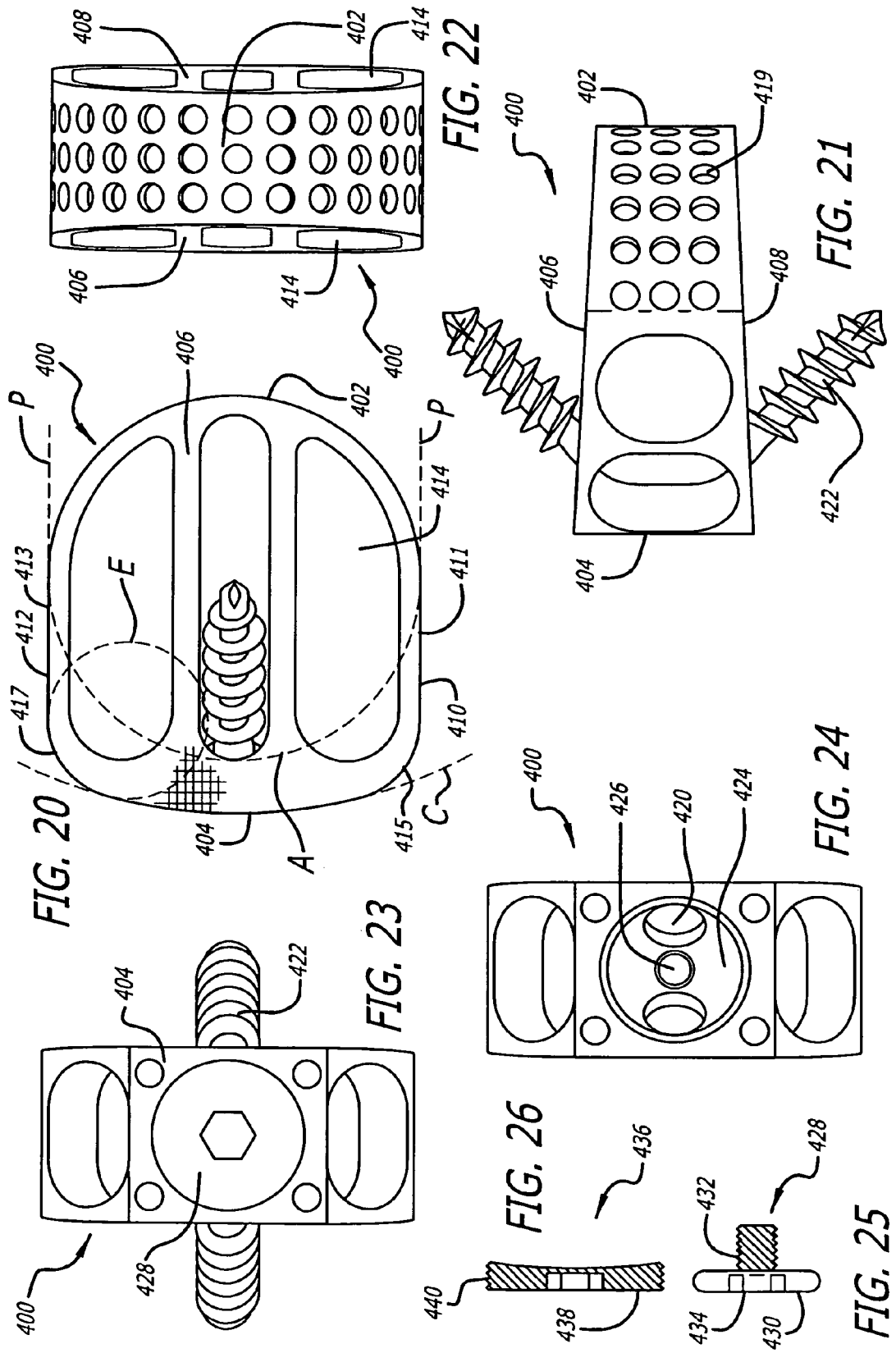

ARTIFICIAL SPINAL FUSION IMPLANT WITH ASYMMETRICAL LEADING END

RELATED APPLICATIONS

This application is a continuation of application Ser. No. 10/112,747, filed Apr. 2, 2002; now U.S. Pat. No. 6,890,355 which claims the benefit of Provisional Application No. 60/281,187, filed Apr. 3, 2001, and Provisional Application No. 60/281,124, filed Apr. 2, 2001; all of which are incorporated by reference herein.

FIELD OF THE INVENTION

The present invention relates generally to interbody spinal implants preferably adapted for placement into an implantation space created across the height of a disc space between two adjacent vertebral bodies for the purpose of correcting spinal disease at that interspace. The spinal implants are made of an implant material that is other than bone and may or may not be resorbable. The implants are adapted such that fusion occurs at least in part through the implants.

DESCRIPTION OF THE RELATED ART

Implants for placement between adjacent vertebral bodies in the spine come in a variety of shapes and sizes and are made of a variety of materials. Such implants for use in human spinal surgery include implants made of selected inert materials, such as titanium, that have a structure designed to promote fusion of the adjacent vertebral bodies by allowing bone to grow through the implant to thereby fuse the adjacent vertebral bodies.

The spinal disc that resides between adjacent vertebral bodies maintains the spacing between those vertebral bodies and, in a healthy spine, allows for relative motion between the vertebrae. At the time of surgery, for example in the instance where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral end plate are relatively inert to new bone growth, the surgeon must work on the end plate to remove at least the outermost cell layers of bone to gain access to the blood-rich, vascular bone tissue within the vertebral body. In this manner, the vertebrae are prepared in a way that encourages new bone to grow into or through an implant that is placed between the vertebral bodies.

Present methods of forming this space between adjacent vertebral bodies generally include the use of one or more of the following: hand held biting and grasping instruments known as rongeurs; drills and drill guides; rotating burrs driven by a motor; osteotomes and chisels, and a double wheel cutter or vertebral interspace preparation device. In particular, the double wheel cutter or vertebral interspace preparation device, as disclosed by Michelson in WO 99/63891, incorporated herein by reference, is adapted for linear insertion, i.e., insertion along a single axis, and without the need to substantially move the device from side to side within the disc space along a second axis. In such a preferred embodiment, the device has at its working end an abrading element having a width generally corresponding to the width of the implant to be implanted.

There is a desire to improve congruity at the interfaces of the implant to the adjacent vertebral bodies, and to achieve stability of the implant. Therefore it is advantageous for the contour of the implants to closely match the implantation space formed between and at least in part into the adjacent vertebral bodies to allow a more uniform load transfer across the implant between the vertebral bodies.

As it is desirable to take advantage of all these benefits, there exists a need for an improved interbody spinal fusion implant made of a material other than bone having a configuration that provides for an improved congruity of the implant to the vertebral bodies and improved implant stability.

SUMMARY OF THE INVENTION

In accordance with the purposes of the present invention, as embodied and broadly described herein, an artificial interbody spinal fusion implant made of a material other than bone is provided for insertion at least in part into an implantation space formed across the height of a disc space between adjacent vertebral bodies of a human spine. The implant includes a leading end for insertion first into the disc space and a trailing end opposite the leading end. The implant has a length from the leading end to the trailing end. The leading end is configured in the shape of approximately one half of a circle from side to side. The implant also includes opposed upper and lower portions between the leading and trailing ends that are adapted to be placed within the disc space to contact and support the adjacent vertebral bodies. The upper and lower portions are non-arcuate along at least a portion of the length of the implant. The upper and lower portions include at least one opening in communication with one another and adapted to hold bone growth promoting material for permitting for the growth of bone from vertebral body to vertebral body through the implant. The implant also includes opposite sides between the upper portion and lower portion, and between the leading and trailing ends. At least one of the opposite sides is at least in part straight along at least a portion of the length of the implant.

In accordance with the purposes of the present invention, as embodied and broadly described herein, an interbody spinal fusion implant made of a material other than bone is provided for insertion at least in part into an implantation space formed across the height of a disc space between adjacent vertebral bodies of a human spine. The implant includes a leading end for insertion first into the disc space and a trailing end opposite the leading end. The implant has a length from the leading end to the trailing end. The leading end is configured from side to side in the shape of approximately one half of a first circle. The trailing end has a radius of curvature of a second circle from side to side. The second circle has a radius greater than the radius of the first circle. The implant also includes opposed upper and lower portions between the leading and trailing ends that are adapted to be placed within the disc space to contact and support the adjacent vertebral bodies. The upper and lower portions include at least one opening in communication with one another and adapted to hold bone growth promoting material for permitting for the growth of bone from vertebral body to vertebral body through the implant. The implant has a maximum width that is greater than one-half of the width of the adjacent vertebral bodies into which the implant is adapted to be inserted.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

FIG. 1 is a top plan view of a vertebral body in the lumbar spine with an implantation space formed to receive a spinal implant having a radius of curvature at the leading end that is less than the radius of curvature of the trailing end of the anterior aspect of the vertebral body between the sides of the implantation space.

FIG. 2 is a side elevation view of two adjacent vertebral bodies in the lumbar spine with the implantation space of FIG. 1 formed across the height of the spinal disc and into the adjacent vertebral bodies.

FIG. 3 is a side perspective view of the implantation space of FIG. 1.

FIG. 4 is a top plan view of a vertebral body in the cervical spine with an implantation space formed to receive a spinal implant having a radius of curvature at the leading end that is less than the radius of curvature of the trailing end of the anterior aspect of the vertebral body.

FIG. 5 is a side elevation view of two adjacent vertebral bodies in the cervical spine with the implantation space of FIG. 4 formed across the height of the spinal disc and into the adjacent vertebral bodies.

FIG. 6 is a side perspective view of the implantation space of FIG. 4.

FIG. 7 is a top plan view of a vertebral body in the lumbar spine and a preferred embodiment of an implant in accordance with the present invention installed into the implantation space of FIG. 1.

FIG. 8 is a side elevation view of two adjacent vertebral bodies with the implant of FIG. 7 installed into the implantation space of FIG. 1 formed across the height of the spinal disc and into the adjacent vertebral bodies.

FIG. 9 is a top plan view of the implant of FIG. 7.

FIG. 10 is a side elevation view of the implant of FIG. 7.

FIG. 11 is a leading end view of the implant of FIG. 7.

FIG. 12 is a trailing end view of the implant of FIG. 7.

FIG. 13 is a top plan view of another preferred embodiment of an implant in accordance with the present invention for use in the implantation space of FIG. 4.

FIG. 15 is a top plan view of one of the members of the implant of FIG. 14.

FIG. 16 is an interior side elevation view of one of the members of the implant of FIG. 14.

FIG. 17 is an exterior side elevation view of one of the members of the implant of FIG. 14.

FIG. 18 is a leading end view of one of the members of the implant of FIG. 14.

FIG. 19 is a trailing end view of one of the members of the implant of FIG. 14.

FIG. 20 is a top plan view of another preferred embodiment of an implant in accordance with the present invention with bone engaging screws.

FIG. 21 is a side elevation view of the implant of FIG. 20.

FIG. 22 is a leading end view of the implant of FIG. 20.

FIG. 23 is a trailing end view of the implant of FIG. 20 with the bone engaging screws and lock installed.

FIG. 24 is a trailing end view of the implant of FIG. 23 without the bone engaging screws and lock installed.

FIG. 25 is a partial cross sectional side view of a preferred embodiment of a bone screw lock in accordance with the present invention for use with the implant of FIG. 20.

FIG. 26 is a cross sectional side view of another preferred embodiment of a bone screw lock in accordance with the present invention.

DETAILED DESCRIPTION OF THE INVENTION

Figure 14:
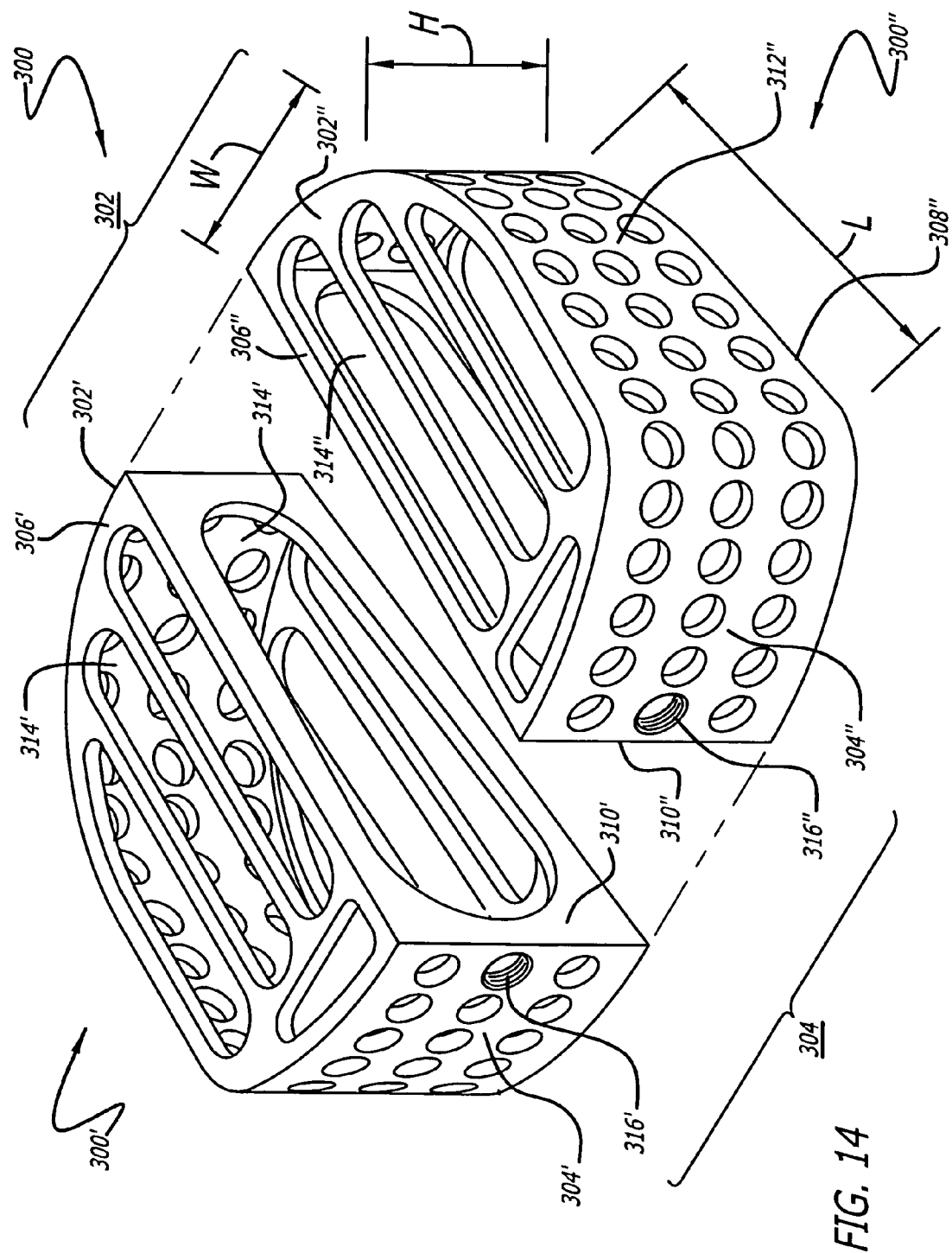
FIG. 14 is a rear perspective view of another preferred embodiment of an implant in accordance with another preferred embodiment of the present invention having two members that are preferably mirror images of one another.

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings. Wherever possible, the same reference numbers will be used throughout the drawings to refer to the same or like parts.

FIGS. 1-3 show an implantation space 50 formed across the height of the space occupied by a spinal disc D and into vertebral bodies V in the lumbar spine. Implantation space 50 is preferably formed with the apparatus and method disclosed by Michelson in U.S. Pat. No. 6,083,228, and WO 99/63891, the disclosures of which are both incorporated herein by reference. The instruments and method are not the subject matter of this application. It is understood that the preparation of the implantation space shown therein are a preferred instrument and method of preparing the implantation spaces and that any method and instrumentation suitable for the purpose may be utilized to prepare the desired implantation space adapted to receive the implants of the present invention.

Implantation space 50 is preferably formed in the endplate region ER in the subchondral bone of the vertebral body V. Implantation space 50 preferably is formed to have a leading edge 52 with a shape from side to side of approximately one-half of a first circle A. The trailing portion 54 of implantation space 50 preferably includes at least a portion of the anterior aspect of the vertebral body having a radius of curvature of a second circle B from side to side. Preferably the radius of circle A is less than the radius of circle B. Implantation space 50 may further include side edges 56, 58. Side edges 56, 58 preferably include at least a straight portion, may be parallel to one another along lines P and form a curved transition with leading edge 52.

FIGS. 4-6 show an implantation space 60 formed across the height of the space occupied by a spinal disc D and into vertebral bodies V in the cervical spine. Implantation space 60 preferably is formed to have a leading edge 62 with a shape from side to side of approximately one half of a first circle A. The trailing portion of implantation space 60 preferably includes at least a portion of the anterior aspect of the vertebral body having a radius of curvature of a second circle C from side to side. Preferably the radius of circle A is less than the radius of circle C. Implantation space 60, however, preferably does not have straight side edges like implantation space 50 because the anterior to posterior depth of cervical vertebral bodies is less than the anterior to posterior depth of lumbar vertebral bodies. Thus, the radius of circle C is smaller in the cervical spine than the radius of circle B in the lumbar spine.

FIGS. 7-12 show an implant 100 in accordance with a preferred embodiment of the present invention. Implant 100 has a leading end 102 for insertion first into the disc space between two adjacent vertebral bodies and a trailing end 104 opposite leading end 102, and opposite sides 110, 112 therebetween. Leading end 102 is preferably configured to match the contour of leading edge 52 of implantation space 50 and trailing end 104 is preferably configured to conform to the contour of the anterior aspect of the vertebral body at trailing portion 54 of implantation space 50. Sides 110, 112 are generally planar and preferably correspond to the configuration of side edges 56, 58 of implantation space 50.

In a preferred embodiment of the present invention, leading end 102, trailing end 104, and opposite sides 110, 112 may have various configurations. Leading end 102 is preferably is in the shape of approximately half a first circle from side to side. Where the implantation space is prepared into the vertebral bodies to have a lip or ridge that is at least in part curved, leading end 102 may be adapted to abut at least that portion of the implantation space.

One or both of sides 110, 112 may also be formed to be at least in part oriented generally parallel to the mid-longitudinal axis of implant 100 and/or to each other. One or both of sides 110,112 may include at least one opening 119 to permit for the growth of bone therethrough and into implant 100, though the invention is not so limited. Further, leading end 102 may be tapered to facilitate insertion of implant 100 between the two adjacent vertebral bodies.

Trailing end 104 preferably forms an arc of a second circle from side to side having a radius greater than the radius of the first circle associated with leading end 102. Preferably, at least a portion of trailing end 104 is adapted to conform to at least a portion of the peripheral contour of the anterior aspect of the vertebral bodies adjacent the disc space into which the implant is adapted to be inserted, though the invention is not so limited.

FIG. 12 shows that implant 100 preferably has a driver opening 116 at trailing end 104 for cooperatively engaging an instrument for installing implant 100 into the implantation space. Driver opening 116 is preferably configured for threaded engagement with an insertion instrument.

FIGS. 8, 10, and 11 show at least a portion of upper and lower surfaces 106, 108 in an angular relationship to each other from trailing end 104 to leading end 102 for allowing for angulation of the adjacent vertebral bodies relative to each other. Preferably, upper and lower surfaces 106, 108 are non-arcuate in a direction along the mid-longitudinal axis of implant 100. Implant 100 preferably has a maximum height that is less than the maximum width of the implant.

As shown in FIG. 9, upper and lower surfaces 106, 108 preferably have at least one opening 114 passing therethrough between leading and trailing ends 102,104, respectively, and opposite sides 110, 112. Openings 114 are preferably adapted to hold bone growth promoting material to permit for the growth of bone from vertebral body to vertebral body through openings 114 and through implant 100. Upper and lower surfaces 106, 108 may also be porous and may include a bone ingrowth surface.

As shown in FIG. 9, the implants described herein may include a bone-engaging surface 118 such as knurling for example. Bone engaging surface 118 is configured to engage the bone of the adjacent vertebral bodies to maintain implant 100 within the adjacent vertebral bodies after implantation. Other preferred embodiments of bone-engaging surfaces may include the surfaces of the implant being roughened, ratcheted, splined, or may include at least one protrusion to penetrably engage the bone of the vertebral bodies. By way of example only, the implants of the present invention may include the surface configuration taught by Michelson in U.S. patent application Ser. No. 09/457,228, entitled "Spinal Implant Surface Configuration," the disclosure of which is incorporated by reference herein.

Bone for use as the base material used to form the implant of the preferred embodiment is specifically excluded for the purpose of this application. Where the implants are for spinal fusion, it is appreciated that they may be adapted to receive fusion promoting substances and/or materials within them such as, but not limited to cancellous bone, bone derived products, or others. In a preferred embodiment, the material of the implant is formed of material other than bone, such as metal including, but not limited to, titanium and its alloys, ASTM material, cobalt chrome, or tantalum, ceramic, various surgical grade plastics, plastic composites, carbon fiber composites, coral, and can include artificial materials which are at least in part bioresorbable.

Upper and lower surfaces that are angled relative to each other, when subsequently implanted into the spine, position the adjacent vertebral bodies in angular relationship to each other to restore the natural curvature of the spine, such as lordosis for example.

The implant may have a selected shape suitable for the intended purpose. For example only, the leading end may be in the shape of approximately one half of a circle from side to side. The sides may be at least in part straight. The trailing end may have any desired shape suitable for the intended purpose and may preferably conform to the anatomical contour of the adjacent vertebral bodies between which the implant is adapted to be inserted.

Implant 100 preferably has a length greater than one-half the depth of the vertebral bodies adjacent the disc space into which the implant is adapted to be inserted as measured between the anterior and posterior aspects of the vertebral bodies. Implant 100 also preferably has a maximum width that is greater than one-half the width of the adjacent vertebral bodies into which the implant is adapted to be inserted.

FIG. 13 shows another preferred embodiment of the present invention for use in the cervical spine generally referred to by the numeral 200. Implant 200 is preferably configured to conform to the shape of implantation space 60 formed in the endplates of adjacent cervical vertebral bodies with instrumentation and methods similar to those used in association with the lumbar spine but modified for use in the cervical spine. Implant 200 may, for example, have a leading end 202 formed to have a shape of approximately one-half a first circle from side to side. Trailing end 204 preferably may be formed as an arc of a second circle from side to side that intersects the curvature of leading end 202 from side to side. The radius of the second circle associated with trailing end 204 is preferably greater that the radius of the first circle associated with leading end 202.

FIGS. 14-19 show an implant 300 in accordance with another preferred embodiment of the present invention adapted for use from the anterior approach to the spine. FIG. 14 shows a rear perspective view of implant 300. Implant 300 includes at least two members 300', 300" that are adapted to be placed side by side with one another. Member 300' is preferably, but need not be a mirror image of member 300". The description of member 300' is equally applicable to member 300". Member 300' has a leading portion 302' for insertion first into the disc space between two adjacent vertebral bodies and a trailing portion 304' opposite leading portion 302'. Member 300' has a top 306', a bottom 308', an interior side 310', and an exterior facing side 312' opposite interior facing side 310'. As used herein, the phrase "interior side" describes the side of the member adapted to be orientated toward the interior side of another member when a pair of members are inserted side by side into the disc space.

Leading portions 302', 302" of each member 300', 300", respectively, form leading end 302 of implant 300 when the members are placed side by side to one another. Leading end 302 of implant 300 is preferably configured in the shape of one-half a first circle from side to side. Trailing end 304, composed of trailing portions 304', 304" when members 300', 300" are placed side by side to one another, may, but need not be formed as an arc of a second circle side to side having a radius greater than a radius of the first circle associated with leading end 302 of implant 300.

Member 300' is placed side by side with member 300" so that a portion of interior side 310' of each member are adjacent one another. Top 306' and bottom 308' preferably have at least one opening 314' passing therethrough between leading and trailing portions 302', 304', respectively, and sides 310', 312'. Openings 314' are adapted to hold bone growth promoting material to permit for the growth of bone from vertebral body to vertebral body through openings 314. Interior side 310' may also include at least one opening 314' passing therethrough configured to permit bone growth between and into adjacent members 300', 300". Member 300' preferably has a maximum width W that is less than approximately one-half the width of the adjacent vertebral bodies into which the member is adapted to be inserted. Also, the combined width of both members 300', 300" is preferably greater than one-half the width of the adjacent vertebral bodies into which the members are adapted to be inserted.

Members 300', 300" provide the added advantage in that each member can be inserted through a smaller space than a single larger implant, to achieve the same effect as the larger implant.

In another preferred embodiment the implant of the present invention may be adapted for use from an anterior approach to the spine and have a maximum width between its sides that is less than one-half of the width of the adjacent vertebral bodies into which the implant is adapted to be inserted. The implant may have a leading end that is shaped as approximately one-half a first circle. The implant may also have a trailing end that forms an arc of a second circle having a radius that is substantially greater than the radius of the first circle associated with the leading end.

In another preferred embodiment, the implant of the present invention may be adapted for use from an anterior approach to the spine and have preferably both the leading and trailing ends in the shape of approximately one half of a circle side to side.

In another preferred embodiment the implant of the present invention may be adapted for use from a posterior approach to the spine and have a trailing end that is preferably at least in part straight from side to side.

FIGS. 20-26 show an implant 400 in accordance with another embodiment of the present invention. Implant 400 is similar to implant 100 and has a leading end 402 in the shape of approximately one-half a first circle A and a trailing end 404 formed as an arc of a second circle C. Implant 400 preferably includes straight portions 411, 413 along at least a portion of sides 410, 412, respectively, that are preferably parallel to each other along lines P. Implant 400 also preferably includes a curved transition from each straight portion 411, 413 of sides 410, 412, respectively, to trailing end 404 to form rounded portions 415, 417, respectively. Rounded portion 415, 417 may be an arc of a third circle E that preferably has a radius less than the radii of circle A associated with leading end 402 and/or circle C associated with trailing end 404.

In a preferred embodiment, implant 400 may be adapted to receive through bone screw receiving holes 420 at trailing end 404 at least a pair of opposed appropriately sized bone screws 422. Bone engaging screws 422 may be aligned or offset from each other. At least one screw 422 engages each of the vertebral bodies adjacent a disc space to be fused and into which implant 400 is implanted. A purpose of the bone screws is to rigidly secure the implant within the vertebral segment. A further purpose is to pull each of the adjacent vertebral bodies toward the implant and towards each other. Trailing end 404 of implant 400 preferably includes a recess 424 having bone screw receiving holes 420 therein and an opening 426 configured to cooperatively receive a locking cap 428 adapted to lock at least one bone screw 422 to implant 400.

As shown in FIG. 25, implant 400 is preferably adapted to receive a lock 428 at trailing end 404 for securing bone engaging screws 422 therein and preventing the screws from backing out. Locking cap 428 has a top 430, a stem 432, and a tool engagement area 434. In use, locking cap cooperatively engages trailing end 404 of implant 400 at opening 426 to lock at least one bone screw to implant 400. If desired, locking cap 428 may include a thread on stem 432 to allow locking cap 428 to rotationally engage implant 400.

FIG. 26 shows another preferred embodiment of a locking cap, generally referred to by the numeral 436. Locking cap 436 includes a top 438 having a thread 440 at its outer perimeter that is adapted to cooperatively engage a corresponding threaded recess in the implant.

The implant, bone screws, and/or locks can be made of a bioresorbable material, including but not limited to plastics and composite plastics. Suitable plastics may include those comprising lactides, galactides, glycolide, capronlactone, trimethylene carbonate, or dioxanone in various polymers, and/or combinations thereof.

By way of example only and not limitation, for use in the lumbar spine, the implants of the present invention may have a depth of approximately, 28-36 mm, a width of approximately, 30-38 mm, and a height (max) of approximately 8-20 mm. The radius of curvature of the leading end may be approximately 15-19 mm and the radius of curvature of the trailing end may be approximately 20-30 mm.

In any of the embodiments of the present invention, the implant may include, be made of, treated, coated, filled, used in combination with, or have a hollow or opening for containing artificial or naturally occurring materials and/or substances suitable for implantation in the human spine. These materials and/or substances include any source of osteogenesis, bone growth promoting materials, bone, bone derived substances or products, demineralized bone matrix, mineralizing proteins, ossifying proteins, bone morphogenetic proteins, hydroxyapatite, genes coding for the production of bone, and bone including, but not limited to, cortical bone. The implant can include at least in part of materials that are bioabsorbable and/or resorbable in the body such as bone and/or bone growth promoting materials. The implant of the present invention can be formed of a porous material or can be formed of a material that intrinsically participates in the growth of bone from one of adjacent vertebral bodies to the other of adjacent vertebral bodies. Where such implants are for posterior implantation, the trailing ends of such implants may be treated with, coated with, or used in combination with chemical substances to inhibit scar tissue formation in the spinal canal. The implant of the present invention may be modified, or used in combination with materials to make it antibacterial, such as, but not limited to, electroplating or plasma spraying with silver ions or other substance. At least a portion of the implant may be treated to promote bone ingrowth between the implant and the adjacent vertebral bodies. The implant of the present invention may be used in combination with a spinal fixation implant such as any object, regardless of material, that can be inserted into any portion of the spine, such as but not limited to interbody spinal implants, structural bone grafts, mesh, cages, spacers, staples, bone screws, plates, rods, tethers of synthetic cords or wires, or other spinal fixation hardware While the shapes of the various aspects of the implant have been described precisely, the scope of the present invention is not so limited and it is readily anticipated that the contours may be interrupted by minor irregularities such as for example only for the purpose of engaging the bone, encouraging the ingrowth or through growth of bone.

While specific innovative features were presented in reference to specific examples, they are just examples, and it should be understood that various combinations-of these innovative features beyond those specifically shown are taught such that they may now be easily alternatively combined and are hereby anticipated and claimed.

What is claimed is:

1. An artificial interbody spinal fusion implant for insertion at least in part into an implantation space formed across the height of a disc space between adjacent vertebral bodies of a human spine, the vertebral bodies having an anterior aspect and a posterior aspect and a depth therebetween, and a width, said implant comprising:

a leading end for insertion first into the disc space and a trailing end opposite said leading end, said implant having a length from said leading end to said trailing end and a mid-longitudinal axis along the length;

opposed upper and lower portions between said leading and trailing ends adapted to be placed at least in part within and across the height of the disc space to contact and support the adjacent vertebral bodies, said upper and lower portions defining a height of said implant, said upper and lower portions being non-arcuate along at least a portion of the length of said implant;

opposite sides between said upper portion and said lower portion, and between said leading and trailing ends, said opposite sides defining a width of said implant, said implant having a maximum width between said opposite sides being less than one-half of the width of the adjacent vertebral bodies into which said implant is adapted to be inserted, each of said opposite sides. being at least in part straight in a direction from said leading end to said trailing end along at least a portion of the length of said implant; and a hollow interior between said upper and lower portions, at least one of said opposite sides including an opening in communication with said hollow interior, said opening having a dimension greater than one-half the length of said implant, said leading end being asymmetrical and curved across the mid-longitudinal axis from one of said opposite sides to another one of said opposite sides;

said implant being manufactured from a material other than bone, said upper and lower portions of said implant including at least one opening in communication with one another for permitting for the growth of bone from vertebral body to vertebral body through said implant.

2. The implant of claim 1, wherein said implant is adapted to be inserted side by side with a second implant into the disc space between the adjacent vertebral bodies, said second implant having a leading end configured in the shape of approximately one quarter of a circle from side to side, the circle having a radius generally equal to the width of said second implant.

3. The implant of claim 1, wherein at least a portion of said leading end has a reduced height to facilitate insertion of said implant between the two adjacent vertebral bodies.

4. The implant of claim 1, wherein said leading end is curved from side to side.

5. The implant of claim 1, wherein said trailing end is curved from side to side.

6. The implant of claim 1, wherein said leading and trailing ends are each curved from side to side.

7. The implant of claim 6, wherein the radius of curvature of said trailing end is greater than the radius of curvature of the leading end of said implant.

8. The implant of claim 1, wherein said at least one opening is between said opposite sides of said implant.

9. The implant of claim 1, wherein said at least one opening is between said leading and trailing ends of said implant.

10. The implant of claim 1, wherein at least one of said opposite sides is at least in part oriented generally parallel to the mid-longitudinal axis of said implant.

11. The implant of claim 1, wherein said opposite sides are at least in part generally parallel one another.

12. The implant of claim 1, wherein at least a portion of said upper and lower portions are in an angular relationship to each other from trailing end to leading end for allowing angulation of the adjacent vertebral bodies relative to each other.

13. The implant of claim 1, wherein said implant has a maximum length less than and approximating the posterior to anterior depth of the vertebral bodies.

14. The implant of claim 1, further comprising a bone engaging surface formed on the exterior of at least said upper and lower portions for engaging the adjacent vertebral bodies, said bone engaging surface including at least one of a protrusion, a ratchet, a spike, a spline, surface roughenings, and knurling.

15. The implant of claim 1, in combination with a bone growth promoting material.

16. The implant of claim 15, wherein said bone growth promoting material is selected from one of bone, bone derived products, demineralized bone matrix, mineralizing proteins, ossifying proteins, bone morphogenetic protein, hydroxyapatite, and genes coding for the production of bone.

17. The implant of claim 1, wherein said implant is treated with a bone growth promoting substance.

18. The implant of claim 1, wherein said implant is at least in part resorbable.

19. The implant of claim 1, in combination with a chemical substance adapted to inhibit scar formation.

20. The implant of claim 1, in combination with an anti-microbial material.

21. The implant of claim 1, wherein at least a portion of said implant is treated to promote bone ingrowth between said implant and said adjacent vertebral bodies.

22. The implant of claim 1, in combination with at least one spinal fixation implant.

23. The implant of claim 1, wherein said trailing end is adapted to receive at least one bone screw adapted to engage at least one vertebral body when inserted through said implant.

24. The implant of claim 23, further comprising a lock for locking at least one bone screw to said implant.

25. The implant of claim 1, wherein each of said upper and lower surfaces of said implant include a plurality of said openings.

26. The implant of claim 1, wherein said opening of said at least one of said sides is generally oval-shaped.

27. The Implant of claim 1, wherein at least one of said sides includes a straight portion along the length of said implant.

28. The implant of claim 27, wherein said opening of said at least one of said sides has a length longer than said straight portion.

29. The implant of claim 1, wherein said opening of said at least one of said sides has a dimension larger than the maximum dimension of any of said at least one openings of said upper and lower portions.

* * * * *

UNITED STATES PATENT AND TRADEMARK OFFICE
CERTIFICATE OF CORRECTION

PATENT NO. : 7,540,882 B2  Page 1 of 1
APPLICATION NO. : 11/089057
DATED : June 2, 2009
INVENTOR(S) : Gary K. Michelson It is certified that error appears in the above-identified patent and that said Letters Patent is hereby corrected as shown below:

On the Title Page, Item (56) References Cited:
U.S. Patent Documents, line 24: change "Aebl" to -- Aebi --; and
Foreign Patent Documents, after line 20: insert -- WO    WO 0168005    9/2001 --.

Column 9, Line 45:
Change "sides. being" to -- sides being --.

Column 11, Line 8:
Change "The Implant" to -- The implant --.

Signed and Sealed this

Fourth Day of August, 2009

JOHN DOLL
*Acting Director of the United States Patent and Trademark Office*